United States Patent
Polito et al.

(10) Patent No.: US 7,297,529 B2
(45) Date of Patent: *Nov. 20, 2007

(54) METHOD AND APPARATUS FOR PERFORMING A LATERAL FLOW ASSAY

(75) Inventors: Alan J. Polito, Danville, CA (US); Richard M. Thayer, Alamo, CA (US); Robert K. DiNello, Hayward, CA (US); George H. Sierra, Concord, CA (US); Dennis Nixon, Merrimack, NH (US); Alan Phillips, Los Altos, CA (US); Stuart Neubarth, Moutain View, CA (US)

(73) Assignee: Relia Diagnostic Systems, LLC, San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/634,331

(22) Filed: Aug. 4, 2003

(65) Prior Publication Data

US 2005/0074899 A1    Apr. 7, 2005

Related U.S. Application Data

(63) Continuation of application No. 09/638,668, filed on Aug. 14, 2000, now abandoned, which is a continuation of application No. 09/199,255, filed on Nov. 23, 1998, now Pat. No. 6,136,610.

(51) Int. Cl.
*C12M 1/00* (2006.01)
*C12M 1/42* (2006.01)
*C12M 1/36* (2006.01)
*C12M 3/00* (2006.01)
*C12M 1/34* (2006.01)

(52) U.S. Cl. .............................. 435/285.2; 435/283.1; 435/286.1; 435/287.1; 435/287.3; 438/171; 429/22; 429/23; 429/26; 429/61; 429/62; 429/90; 356/38; 356/244; 123/406.11; 123/406.66; 123/407

(58) Field of Classification Search ............. 435/283.1, 435/285.2, 286.1, 287.2, 287.3; 29/38, 244; 123/406.11, 406.66, 407; 318/662; 356/38, 356/244; 388/919; 429/22, 23, 26, 61, 62, 429/90; 438/171; 505/192

See application file for complete search history.

(56) References Cited

U.S. PATENT DOCUMENTS 4,626,684 A   12/1986   Landa
4,822,566 A    4/1989   Newman (Continued)

FOREIGN PATENT DOCUMENTS

WO        WO 0058730        10/2000

*Primary Examiner*—Jeffrey Siew
*Assistant Examiner*—J. Hines
(74) *Attorney, Agent, or Firm*—Cooley Godward Kronish LLP

(57) ABSTRACT

An embodiment of the present invention provides a method for performing a lateral flow assay. The method includes depositing a sample on a test strip at an application region, detecting a first detection signal arising from the test strip in the first detection zone, and generating a baseline for the first measurement zone by interpolating between values of the detection signal outside of the first measurement zone and inside of the first detection zone. The method may include locating a beginning boundary and an ending boundary for the first measurement zone on the test strip. Additional detection zones having measurement zones may also be incorporated with the embodiment.

13 Claims, 8 Drawing Sheets

U.S. PATENT DOCUMENTS

| | | |
|---|---|---|
| 5,049,487 A | 9/1991 | Phillips et al. |
| 5,344,754 A * | 9/1994 | Zweig .......................... 435/4 |
| 5,356,785 A | 10/1994 | McMahon et al. |
| 5,418,143 A | 5/1995 | Zweig |
| 5,554,531 A * | 9/1996 | Zweig ..................... 435/286.1 |
| 5,580,794 A | 12/1996 | Allen |
| 5,753,517 A | 5/1998 | Brooks et al. |
| 6,136,610 A * | 10/2000 | Polito et al. ................ 436/514 |

* cited by examiner

METHOD AND APPARATUS FOR PERFORMING A LATERAL FLOW ASSAY

CROSS-REFERENCE TO RELATED APPLICATIONS

This application is a continuation of U.S. patent application Ser. No. 09/638,668 by Polito et al., filed Aug. 14, 2000, and now abandoned, which is a continuation of U.S. patent application Ser. No. 09/199,255, filed Nov. 23, 1998, now U.S. Pat. No. 6,136,610, from which applications priority is claimed pursuant to 35 U.S.C. § 120 and which applications are incorporated herein by reference in their entireties.

BACKGROUND OF THE INVENTION

1. Field of the Invention

The present invention pertains to a method and apparatus for performing and analyzing a lateral flow assay. More specifically, the invention provides a method and apparatus for determining the amount of an analyte present in a subject sample.

2. Description of Related Art

Immunoassay technology provides simple and relatively quick means for determining the presence of analytes in a subject sample. The information provided from immunoassay tests are often critical to patient care. Assays are typically performed to detect the presence of particular analytes, such as antibodies that are present when a human subject has a particular disease or condition. Assays practiced under the known art are numerous, and may include assays for diseases such as *H. pylori*, AIDS or conditions such as pregnancy.

The advancement of immunoassay technology now allows for assay tests to be performed without the complex and expensive equipment used in hospitals and laboratory settings. Devices for performing assays are now available for home or point of care use to quickly determine the presence of a disease or condition. Such devices typically provide qualitative results for the analyte-or condition being tested for. Examples of such devices include strips that become visually distinguishable when the analyte being sought is detected.

However, devices for qualitative analysis of assays are often prone to user error, and lack the accuracy of sophisticated equipment that perform and analyze the assays in hospitals and laboratories. For instance, assay devices often require the user to visually interpret an ongoing chemical reaction. In some applications, if the user mis-times reading the assay device by even a few minutes, the result of the assay may turn from negative to positive. Still, other devices fail to sufficiently distinguish positive from negative results.

Readers are provided in the known art for determining or analyzing the results of assays more accurately. In general, readers provide an improvement in that they may analyze an assay result, thereby removing subjective factors that cause human error. However, whereas readers may reduce operator subjectivity in reading or interpreting assay results, they do not help to control for or help mitigate other sources of assay variability. Such sources may include variability introduced by incorrect assay run times, uncontrolled reaction temperatures, or other possible operator-induced variability.

The present invention addresses these and other shortcomings of the known art.

SUMMARY OF THE INVENTION

It is therefore an object of the invention to provide a method and apparatus for performing an assay in a variety of settings, such as point of care or near patient care and small laboratory settings.

It is another object of the invention to provide a method and apparatus that quantitatively analyzes results of a lateral flow assay to a high degree of accuracy.

Another object of the invention is to provide a method and apparatus for precisely controlling the timing of a lateral flow assay for more accurate results.

Another object of the invention is to provide a method and apparatus for storing assay tables that may be selected to analyze multiple lateral flow assays performed on a test strip.

Another object of the invention is to provide a method and apparatus to execute an algorithm that accurately analyzes the results of a lateral flow assay performed on a test strip.

And still another object of the invention is to provide a method and apparatus to execute an algorithm that generates a baseline for the strip to determine the results of a lateral flow assay.

With these objects in mind, an embodiment of the present invention provides a method for performing a lateral flow assay. The method includes depositing a sample on a test strip at an application region, detecting a first detection signal arising from the test strip in the first detection zone, and generating a baseline for the first measurement zone by interpolating between values of the detection signal outside of the first measurement zone and inside of the first detection zone. The method may include locating a beginning boundary and an ending boundary for the first measurement zone on the test strip. Additional detection zones having measurement zones may also be incorporated with the embodiment.

In another embodiment of the present invention, a method for performing a lateral flow assay includes providing a test strip on a cartridge, where the test strip includes a first analyte binding agent coupled to a detection agent and a second analyte binding agent. The method further includes depositing a sample on an application region of the test strip, where at least a portion of the sample binds to the first analyte binding agent coupled to the detection agent to form a first analyte binding agent complex, the first analyte binding agent complex moving by lateral flow to a first detection zone that includes a measurement zone, where at least a portion of the first analyte binding agent complex binds to the second analyte binding agent in the first measurement zone to form a second complex. In addition, the method also includes detecting an intensity of a first detection signal arising in the first detection zone, generating a baseline of signal intensity from the first measurement zone, and quantifying a value of signal intensity representative of the second complex with respect to the baseline.

In another embodiment of the present invention, a method for performing a lateral flow assay includes applying an electrical potential across a pair of spaced apart electrical leads to create an electrical field. The method further includes introducing a sample into the electrical field to induce a change in the electrical field, the sample being spaced from the spaced apart electrical leads. The method then provides for initiating timing of the lateral flow assay upon detecting the change in the electrical field.

In another preferred embodiment, a method for performing a lateral flow assay includes depositing a sample on a test strip of a cartridge at an application region of the test strip, the test strip including a first detection zone with a first measurement zone. The method further includes inserting the cartridge in a housing having a processor and memory resources for storing a plurality of assay tables, selecting an assay table from a plurality of assay tables to perform the lateral flow assay on the test strip, detecting an intensity of a detection signal arising from a first detection zone of the test strip that includes the first measurement zone, and quantifying a value of signal intensity for the first detection zone using a parameter from the assay table selected from the plurality of assay tables.

Another embodiment of the present invention provides an apparatus for performing a lateral flow assay. The apparatus includes a housing having a receptacle for retaining a test strip that receives a sample. The apparatus also includes a sensor for detecting a first detection signal arising from a first measurement zone of the test strip. A processor and memory resources generates the baseline for the first measurement zone by interpolating between values of the detection signal outside of the first measurement zone and inside of the first detection zone.

Another embodiment of the present invention provides an apparatus for performing a lateral flow assay that includes a pair of spaced apart electrical leads contained within a receptacle of a housing. The electrical leads receive an electrical potential to create an electrical field. A test strip is contained within the receptacle, the test strip being in sufficient proximity to the electrical leads to induce a change in the electrical field upon receiving a sample.

DESCRIPTION OF THE PRESENTLY PREFERRED EMBODIMENTS

This application hereby incorporates U.S. patent application entitled "Improved Lateral Flow Assays," naming Alan Polito, Richard Thayer, Robert DiNello, and George Sierra as inventors, filed Nov. 23, 1998.

Figure 1:
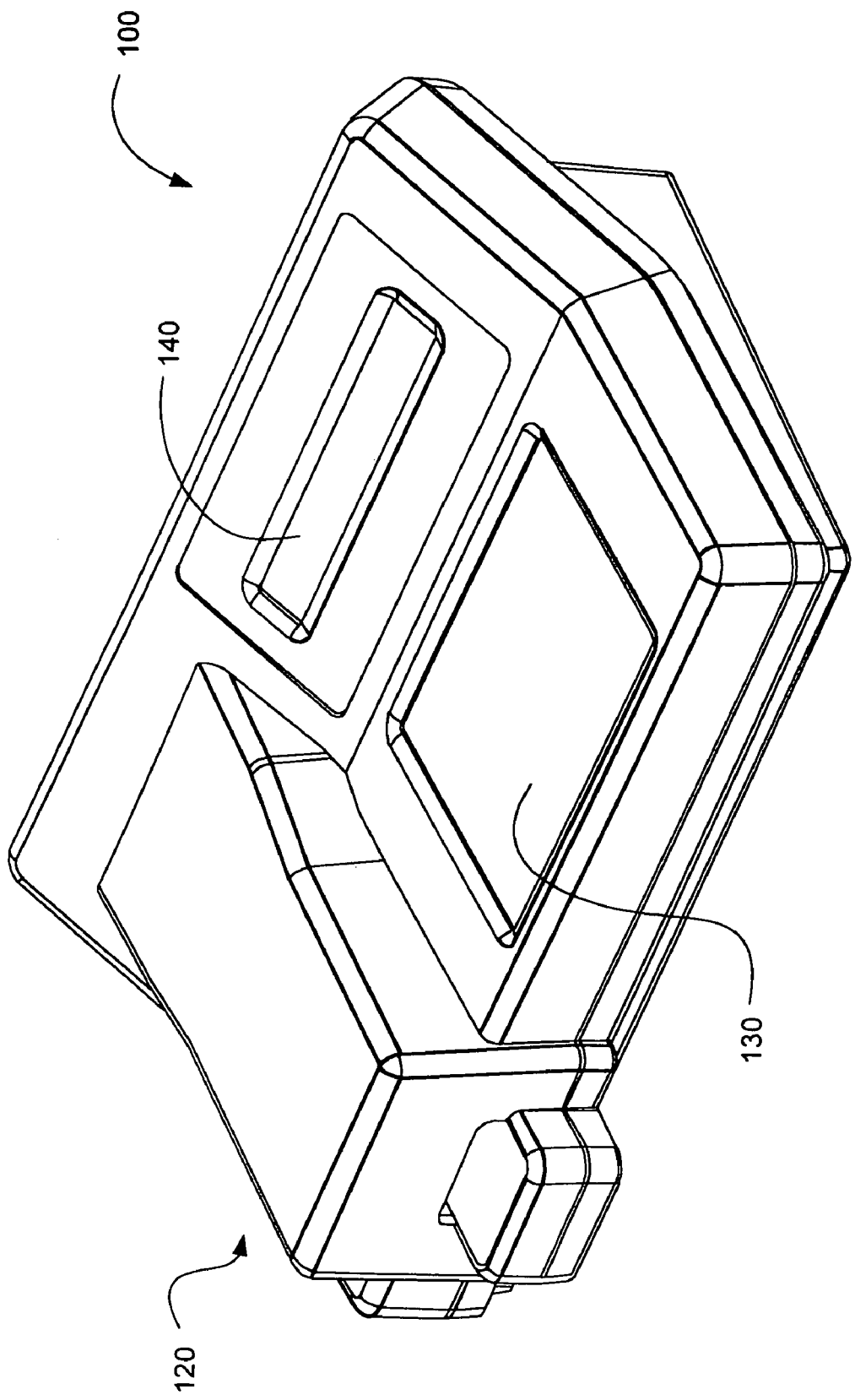
FIG. 1 is an isometric view of a reader under the principles of this invention.

Now turning to the drawings, FIG. 1 shows a preferred embodiment of this invention to include a rapid assay reader 100 for performing and analyzing lateral flow assays. The reader 100 includes a cartridge receptacle 120 for receiving a cartridge having a test strip. A computer system, such as a processor and memory resources, is contained within the reader 100 to control and analyze the assay. The computer system is coupled to an input device such as a keyboard 130 and an output device such as a display 140 to allow for user interaction in performing the assay. The reader 100 may include a battery and/or may be adapted to couple to an AC power supply. A serial port or any other communication outlet may also be provided to upload or download software to and from the computer system contained within the reader 100. Steps included in performing an assay under this invention include conducting the assay on a strip (shown in FIG. 2), and analyzing or interpreting the results of the assay conducted on the strip.

Figure 2:
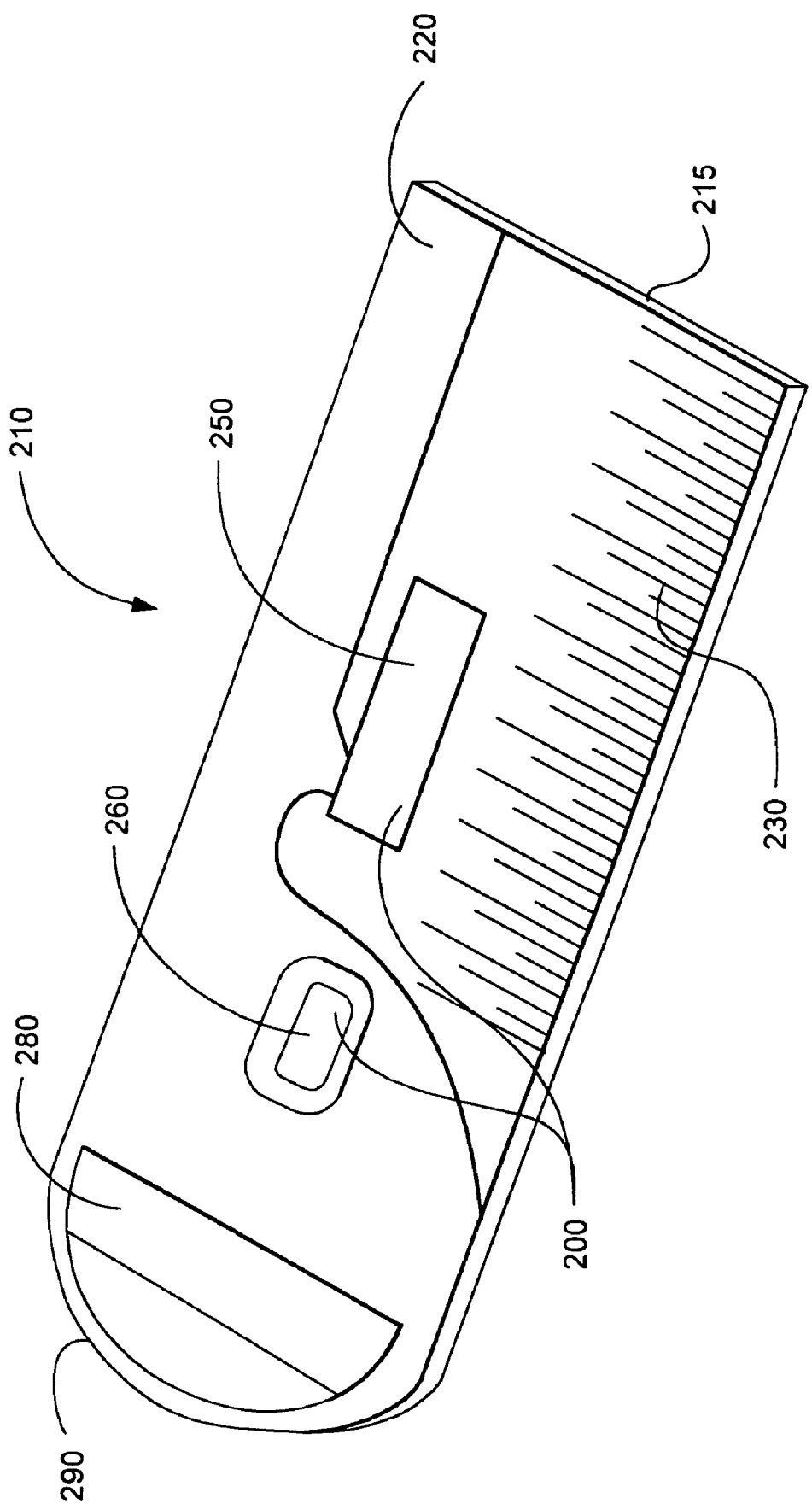
FIG. 2 is an isometric view of the cartridge having a test strip of a preferred embodiment.

FIG. 2 shows in detail a cartridge 210 of a preferred embodiment, dimensioned to be received by the cartridge receptacle 120 (shown by FIG. 1). The cartridge 210 includes a front end 215 that inserts into the cartridge receptacle 120, and a back end 290 that includes a handling surface 280. A test strip 200 for performing a lateral flow assay is encased within the cartridge 210. Cartridge 210 may include a sensor code for communicating with the computer system of the reader 100 on a top surface 220. Preferably, the sensor codes are bar codes 230 that communicate with a bar code reader (shown as second optical sensor 410 in FIG. 4) within the cartridge receptacle 120.

The test strip 200 is exposed through the submerged openings of the cartridge 210 to provide an application region 260 in proximity to the back end 290, and an assay region 250 in proximity to the front end 215. The assay region 250 is dimensioned with respect to the cartridge receptacle 120 so that a portion of the cartridge 210 containing the application region 260 extends from the reader 100 when the cartridge 210 and reader are coupled. A sample may be deposited onto the test strip 200 at the application region 260 to transfer by lateral flow to the assay region 250. A protective layer (not shown) over the assay region 250 protects the sample and chemical constituency of the strip from contamination and evaporation.

The sample deposited on the test strip 200 may comprise analytes. The term, "analyte," as used herein, refers to the molecule or compound to be quantitatively determined. Examples of analytes include proteins, such as hormones and other secreted proteins, enzymes, and cell surface proteins; glycoproteins; peptides; small molecules; polysaccharides; antibodies (including monoclonal or polyclonal Ab); nucleic acids; drugs; toxins; viruses or virus particles; portions of a cell wall; and other compounds possessing epitopes. The analyte of interest preferably comprises an immunogenic portion, meaning that antibodies (as described below) can be raised to that portion of the analyte of interest.

In a preferred embodiment, the test strip 200 may also comprise a population of first analyte binding agent, and optionally an analyte non-specific agent, coupled to a detection agent. In another preferred embodiment, the test strip 200 may also comprise two or more populations. For example, there may be a first population of first analyte binding agent coupled to a detection agent, and a second population of an analyte non-specific agent coupled to a detection agent.

Analyte non-specific agent is defined as an agent non-specific to the analyte of interest. The first analyte binding agents are agents that specifically bind to the analyte of interest. In a preferable embodiment, the first analyte binding agents are antibodies to the analyte of interest. In another preferable embodiment, if the analyte of interest is an antibody of known specificity, the population may comprise the antigen against which the analyte-antibody is directed. The antibodies can be monoclonal antibodies or polyclonal antibodies. The term "antibody", as used herein, also refers to antibody fragments that are sufficient to bind to the analyte of interest. Alternatively, in a preferable embodiment, molecules that specifically bind to the analyte of interest, such as engineered proteins, peptides, haptens, and lysates containing heterogeneous mixture of antigens having analyte binding sites, may also be used.

Different detection agents may be employed with different populations of first and/or second analyte binding agents and analyte non-specific agent coupled to a detection agent. This situation may arise, for example, when it is desired to assay two different analytes of interest on the same test strip. Use of two different detection agents facilitates detection of the two different analytes of interest. For example, when the detection agent is a fluorescent agent, the detection agents may be selected to fluoresce at different wavelengths.

In a preferred embodiment, the detection agent is a particle. Examples of particles useful in the practice of the invention include, but are not limited to, colloidal gold particles; colloidal sulphur particles; colloidal selenium particles; colloidal barium sulfate particles; colloidal iron sulfate particles; metal iodate particles; silver halide particles; silica particles; colloidal metal (hydrous) oxide particles; colloidal metal sulfide particles; colloidal lead selenide particles; colloidal cadmium selenide particles; colloidal metal phosphate particles; colloidal metal ferrite particles; any of the above-mentioned colloidal particles coated with organic or inorganic layers; protein or peptide molecules; liposomes; or organic polymer latex particles, such as polystyrene latex beads. Preferable particles are colloidal gold particles. The size of the particles may be related to porosity of the membrane strip: the particles are preferably sufficiently small to be transported along the membrane by capillary action of fluid.

Colloidal gold may be made by any conventional means, such as the methods outlined in G. Frens, 1973 Nature Physical Science, 241:20 (1973). Alternative methods may be described in U.S. Pat. Nos. 5,578,577, 5,141,850; 4,775,636; 4,853,335; 4,859,612; 5,079,172; 5,202,267; 5,514,602; 5,616,467; 5,681,775.

The selection of particle size may influence such factors as stability of bulk sol reagent and its conjugates, efficiency and completeness of release of particles from the test strip, speed and completeness of the reaction. Also, particle surface area may influence stearic hindrance between bound moieties.

The particles may be labeled to facilitate detection. Examples of labels include, but are not limited to, luminescent labels; colorimetric labels, such as dyes; fluorescent labels; or chemical labels, such as electroactive agents (e.g., ferrocyanide); enzymes; radioactive labels; or radiofrequency labels. The number of particles present in the test strip may vary, depending on the size and composition of the particles, the composition of the test strip and membrane strip, and the level of sensitivity of the assay.

Also coupled to the detection agent may be a analyte non-specific agent. This agent is selected for its ability to bind to substances other than the analyte of interest. For example, if the analyte of interest is an antibody to *H. Pylori*, then the analyte non-specific agent may be an antibody to an antigen not found, or rarely found, in the antibody to *H. Pylori*. This binding may be specific for a substance other than the analyte of interest or non-specific for such a substance.

In a preferable embodiment, the analyte non-specific agent may be antibodies, more preferably rabbit IgG. The antibodies can be monoclonal antibodies or polyclonal antibodies. The term "antibody", as used herein, also refers to antibody fragments that are sufficient to bind to the analyte of interest. Alternatively, preferably, molecules such as engineered proteins having non-specific binding sites non-specific for the analyte of interest, can also be used. In another embodiment, a receptor that non-specifically binds to ligands other than the analyte of interest can be used, and vice versa. Finally, the analyte non-specific agent may be an antigen, another organic molecule, or a hapten conjugated to a protein non-specific for the analyte of interest. Descriptions of other suitable analyte non-specific agents may be found in U.S. Pat. No. 5,096,837, and include IgG, BSA, other albumins, casein, globulin, and immunoglobulin.

In a preferable embodiment, the analyte non-specific agent comprises a control binding agent. Control binding agents are selected so as to bind specifically to molecules other than molecules that specifically bind to the analyte of interest. In this way, these control binding agents can bind in control binding zones, as discussed below. Substances useful as control binding agents include those substances described above as useful as first analyte binding agents. In a preferable embodiment, the control binding agent comprises rabbit anti-dinitrophenol (anti-DNP) antibody. Additional beneficial characteristics of control binding agents include, but are not limited to stability in bulk, non-specificity for analyte of interest, reproducibility and predictability of performance in test, molecular size, and avidity of binding to the control agent.

One or more of the substances discussed above as suitable first analyte binding agents may be used as second analyte binding agents in one or more measurement zones on the strip 200. The measurement zone may be either a control zone or an analyte binding zone. In a preferable embodiment, a second analyte binding agent is an antigen recognized by the analyte of interest, which is an antibody. The second analyte binding agent may also be the antigen or even a second antibody specific for the analyte (antibody) of interest. In another preferable embodiment, the analyte of interest is an antigen. The second analyte binding agent, which is an antibody, may be directed against a different epitope of the analyte compared to the first analyte binding agent, when the latter is also an antibody. Alternatively, when the analyte is an antigen with multiple copies of the same epitope, the second analyte binding agent may be directed against the same epitope as the first analyte binding agent.

Control agents, present in the control binding zones, bind specifically to the control binding agent to form a control binding pair. Thus, control agents are those substances that may specifically bind to the control binding agents disclosed herein. A particular advantage of the control binding pairs according to the invention is that they are internal controls—that is, the control against which the analyte measurement results may be compared is present on, the individual test strip. Therefore, the controls according to the invention may be used to correct for strip-to-strip variability. Such correction would be impractical with external controls that are based, for example, on a statistical sampling of strips. Additionally, lot-to-lot, and run-to-run, variations between different test strips may be minimized by use of control binding agents and control agents according to the invention. Furthermore, the effects of non-specific binding may be reduced. All of these corrections would be difficult to accomplish using external, off-strip, controls.

During the assay, the analytes from the sample and the first analyte binding agent coupled to the detection agent may combine on the test strip with second analyte binding agents in the measurement zones. This combination results in a concentration of compounds that may interrupt the continuous intensity of a signal arising from the test strip 200. The compounds may be formed from a combination of above-mentioned analytes and reagents, including antibodies, detection agents, and other particles associated with the analyte binding zone and/or control zone. Based on the particular assay being performed, the control binding zones may be selectively implemented to achieve an appropriate dynamic range which may be linear or non-linear. The respective quantitative values of the high and low control may in turn be fitted to provide a standard curve, which may be used as a calibration parameter to determine a quantitative value for the analyte binding zone. Once the amount of control agent has been quantified (such as in terms of Density of Reflection, discussed below), the amount may then be mapped onto another more meaningful measurement scale, such as Relative Intensity (RI). The RI value may also be assigned concentration values of analytes of interest. In this way, other meaningful units measurements such as number of copies of analytes present or the concentration of analytes present may be read from the standard curve. Finally, signal to cutoff values (S/CO) above which cutoff values the assay result is considered positive may also be derived from the RI value.

During performance of the assay, a measurement zone may comprise a concentration of compounds that measurably affect a signal arising from the strip after the sample is added to the strip. A signal may arise when analytes present in the sample bind to a moiety comprised of the analyte binding agent and analyte non-specific agent coupled to the detection agent, and are further caused to bind to second analyte binding agents and analyte non-specific agents coupled to the detection agents present in the measurement zone to form concentrated regions of compounds. Still further, the compounds in the measurement zones may also be formed from combining a first population of analyte binding agents existing on the application region 260 with an analyte in the sample, and/or combining the first population of analyte binding agents with a second analyte binding agent existing on the assay region 250 of the test strip. The first population of analyte binding agents may also include control binding agents that bind with control agents in the control zones once the sample is provided to the application region 260.

A detection zone is a region on the strip which contains one or more measurement zones. The signal arising from the detection zone corresponding to a concentration of compounds is termed a detection signal. A baseline is an approximation, or average, of the signal arising from any portion of the strip, excluding detection signals. In a preferred embodiment, the signal and detection signals of the strip are reflectance based measurements. As such, one or more measurement zones contain concentrated quantities of compounds or complexes that form relative dark regions against a highly reflective or substantially white surface of the test strip 200. In alternative variations, the detection signal may arise from alternative compounds such as those using fluorescent or radioactive agents. In such instances, the signal of the baseline may represent an average value of similar signal on the strip excluding regions containing the measurement zones. In any variation, sensors within the reader 100 may be used to measure the detection signal arising from the measurement zones relative to the baseline.

As will be described in greater detail, the present invention improves over the known art by determining the baseline across one or more detection zones of the strip in the presence of variations in the background signal. Each detection zone is preferably located such that an automatic or semi-automatic analytical instrument, or a human reader, may determine certain results of the lateral flow assay. Once the baseline in each detection zone is determined, the measurement zones may be quantified and/or compared with respect to the baseline. Values of the measurement zones corresponding to the respective concentration of compounds may then be compared with one another to detect the presence of antigens in sample.

In a preferred embodiment, the test strip 200 is formed from a high binding membrane having a substantially white reflective background, including films such as nitrocellulose. If present, the analytes in the sample react with first analyte binding agent coupled to a detection agent, and with second analyte binding agents in the analyte binding zones of the assay region 250 to give rise to compounds in a first measurement zone. The compounds are light absorbing compounds that affect the overall reflection intensity of the assay region 250. Preferably, the addition of the sample carries from the application region to the assay region 250 control binding agents coupled to detection agents that combine with control agents in the control binding zones. In a specific application, the addition of the sample carries from the application region 260 the analyte binding agent and analyte non-specific agent bound to the detection agent and further combines with control agents in the control binding zone. In this manner, the measurement zones corresponding to the control binding zones each contain a relatively known quantity of the light absorbing compounds that create a second and third measurement zone. The reflective surface of the strip 200 detecting regions excluding the effect of the measurement zones is the baseline of a preferred embodiment. Values may be assigned to the measurement zones formed from the control and/or analyte binding zones based on the intensity of reflection of the respective measurement zone with respect to the baseline. In a preferred embodiment, the values of the measurement zones forming a high and low control zone are normalized to a predetermined value, such as one and three. A relative intensity curve may then be fitted between the values of the high and low control binding zones, as opposed to a standard curve which uses the absolute unit value of the high and low control. The concentration of light absorbing compounds in the measurement zone of the analyte binding zone may then be quantified by placing the value of the reflection intensity onto the relative intensity curve defined by the high and low control values. The presence of analytes that are the subject of the assay may be indicated when the concentration value of analytes in the measurement zone of the analyte binding zone exceeds the cut-off value implemented with the assay.

Under this invention, the sample may include whole blood, serum, plasma, urine, or other biological samples associated with performing assays on humans. The invention may also provide for non-human samples, including samples originating from livestock or food products, as well as veterinary samples. The analytes present on the test strip 200 and the compounds formed with the sample depend in part on the type of sample provided.

The test strip 200 of a preferred embodiment provides five measurement zones comprised from three analyte binding zones and two control binding zones. Each analyte binding zone may be implemented to indicate the presence of analytes to such diseases such as *H. pylori*, AIDS, herpes, and hepatitis. Greater or fewer analyte binding zones or control binding zones are also contemplated by this invention. A preferred embodiment may also be employed to detect the presence of food contamination, such as *E. Coli* or *Salmonella*.

Figure 3:
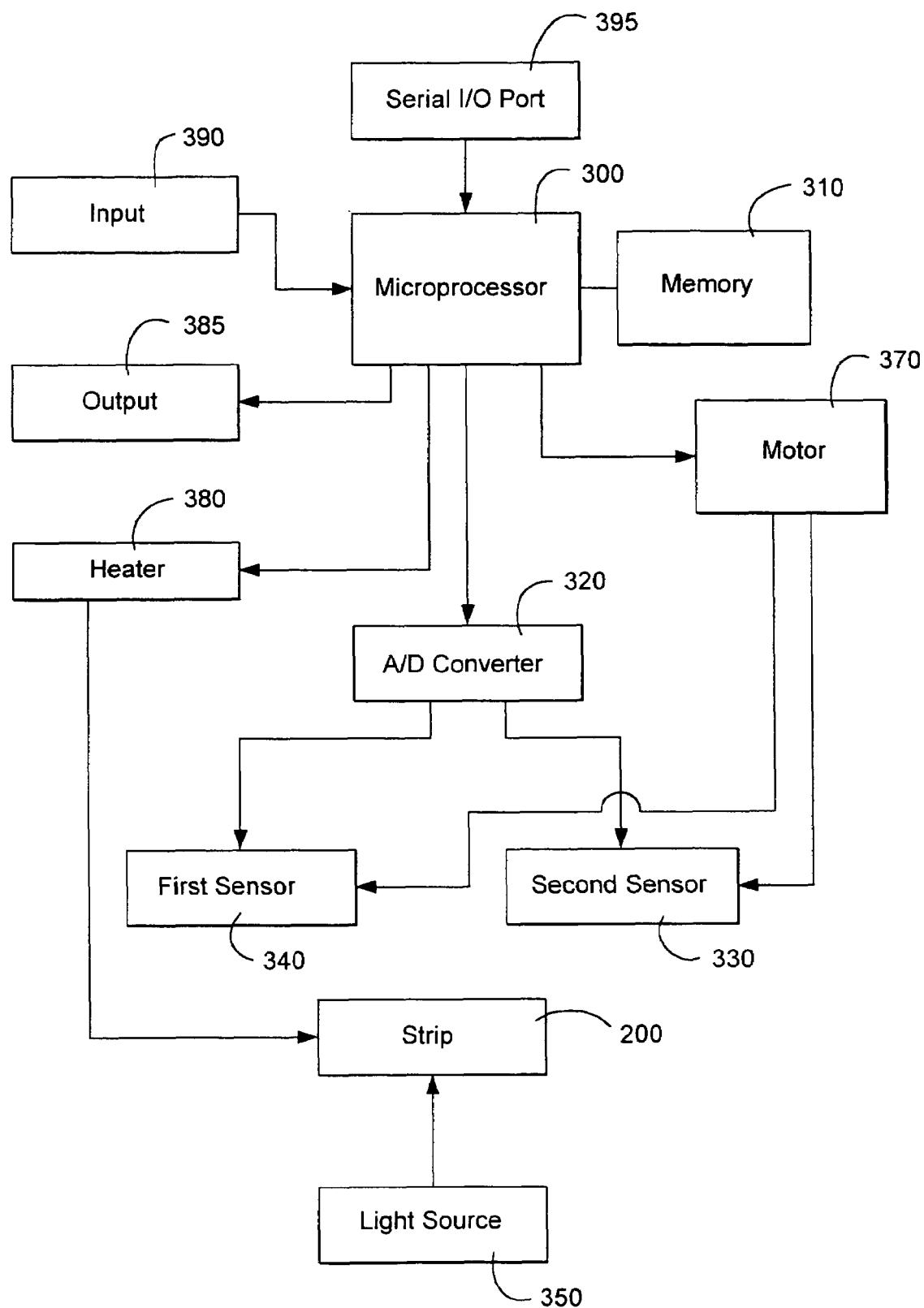
FIG. 3 is a block diagram of a preferred embodiment of this invention.

FIG. 3 is a block diagram showing general components of the reader 100. The computer system of a preferred embodiment is shown to comprise a processor 300 having memory resources 310. As will be described in greater detail, the memory resources 310 stores a plurality of assay tables, with each assay table having parameters and fields suited for a particular assay. The processor 300 receives parameters from the memory resources 310 and executes an algorithm for controlling and analyzing the assay. The processor 300 may also receive parameters or prompts from the input device 390, which may include a keyboard 130, or other suitable devices. An output 385 may prompt the user for information or provide the results of the assay. The output 385 may include the display 140, or a printer, or other audio/visual devices. The processor may also receive input information or provide output information through a serial port 395. The serial port 395 may comprise an infrared port for transferring information between the reader 100 and an external computer, but may also include other known serial ports such as a pin connector or modems. Information that may be provided to the computer system may include parameters that reconfigure the assay tables of the memory resources. The information may be provided through the input device 390, serial port 395, or alternatively through a replacement memory chip such as an insertable memory chip.

As shown by FIG. 3, a preferred embodiment provides that the processor 300 is linked via an analog-digital converter 320 to a first and second sensors 340 and 330. The analog-digital converter 320 converts analog signals from the optical sensors into voltage counts for the processor 300. In alternative embodiments, the analog-digital converter converts signals from a sensor that detects alternative detection signals, such as fluorescence, radiation, magnetic flux, or any other detection signal detectable with a sensor. One of the sensors may be used to input information to the computer system that is contained on detectable codes on the surface 220 of the cartridge 210. In a preferred embodiment, the first and second sensors are light sensors for measuring the reflection intensity arising from the strip 200. As such, a preferred embodiment may include a light source 350 that enhance the detectable reflectance arising from the strip. The processor 300 may couple to a heater 380 that heats the sample to a predetermined temperature, thereby increasing the accuracy and speed of the assay. As will be explained below, the processor 300 controls the temperature and incubation time for the assay. In this manner, the assay may be heated at an optimal temperature and duration. A motor 370 also couples to the processor and provides a preferred mechanism for scanning the first and second sensors 340 and 330 across the test strip 200 and/or cartridge 210.

Figure 4:
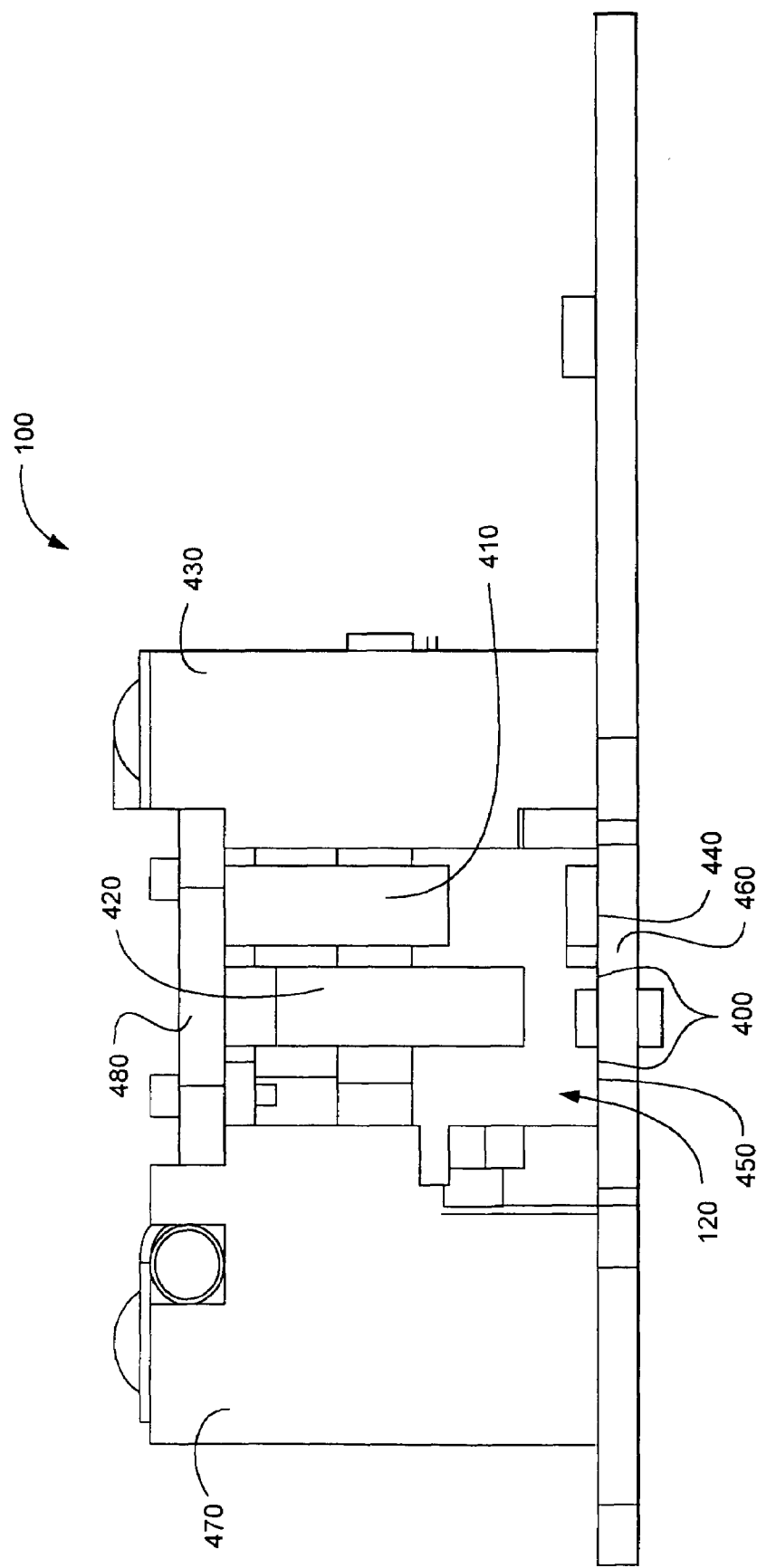
FIG. 4 is a front view of the reader of a preferred embodiment.

FIG. 4 is a front view of the reader 100 detailing a preferred embodiment of the invention. As shown by FIG. 4, the cartridge receptacle retains the cartridge 210 in position to access the test strip 200 (of FIG. 2) to the associated components. The cartridge receptacle 120 also includes a top printed circuit board 480 and a left sidewall 470 and a right side wall 430. The top printed circuit board 480 and sidewalls 470 and 430 may combine to cover and protect the assay region 250 of the test strip 200 from contamination or unwanted elements that may otherwise affect the performance of the assay. A first optical sensor 420 extends from the top printed circuit board 480 of the cartridge receptacle 120 and aligns over the assay region 250 of the test strip 200. The first optical sensor 420 measures the reflectivity of the assay region 250 once the assay is initiated. The light source may be used with either optical sensor to illuminate the test strip 200. A second optical sensor 410 may be used to read bar codes 230 provided on the top surface 220 of the cartridge 210 (as shown by FIG. 3). FIG. 4 shows that the first optical sensor 420 and second optical sensor 410 of a preferred embodiment are vertically offset with respect to one another to compensate for the elevation difference between the bar code 230 on the cartridge and the assay region 250 exposed within the cartridge. The cartridge receptacle 120 may mount to a bottom printed circuit board 460 to couple the components contained therein with the computer system.

FIG. 4 further shows a first pad 440 and second pad 450 positioned on the bottom printed circuit board 460 to form an autostart trigger 400. As will be discussed in greater detail, the autostart trigger 400 is coupled to the computer system 300 (FIG. 3) and associated circuitry to detect the presence of the first drop of the sample deposited on the application region 260. Among other advantages, the autostart trigger 470 improves in part over the prior art in it enables a coupled timer to initiate at an exact moment when the sample is deposited on the application region 260.

Figure 5:
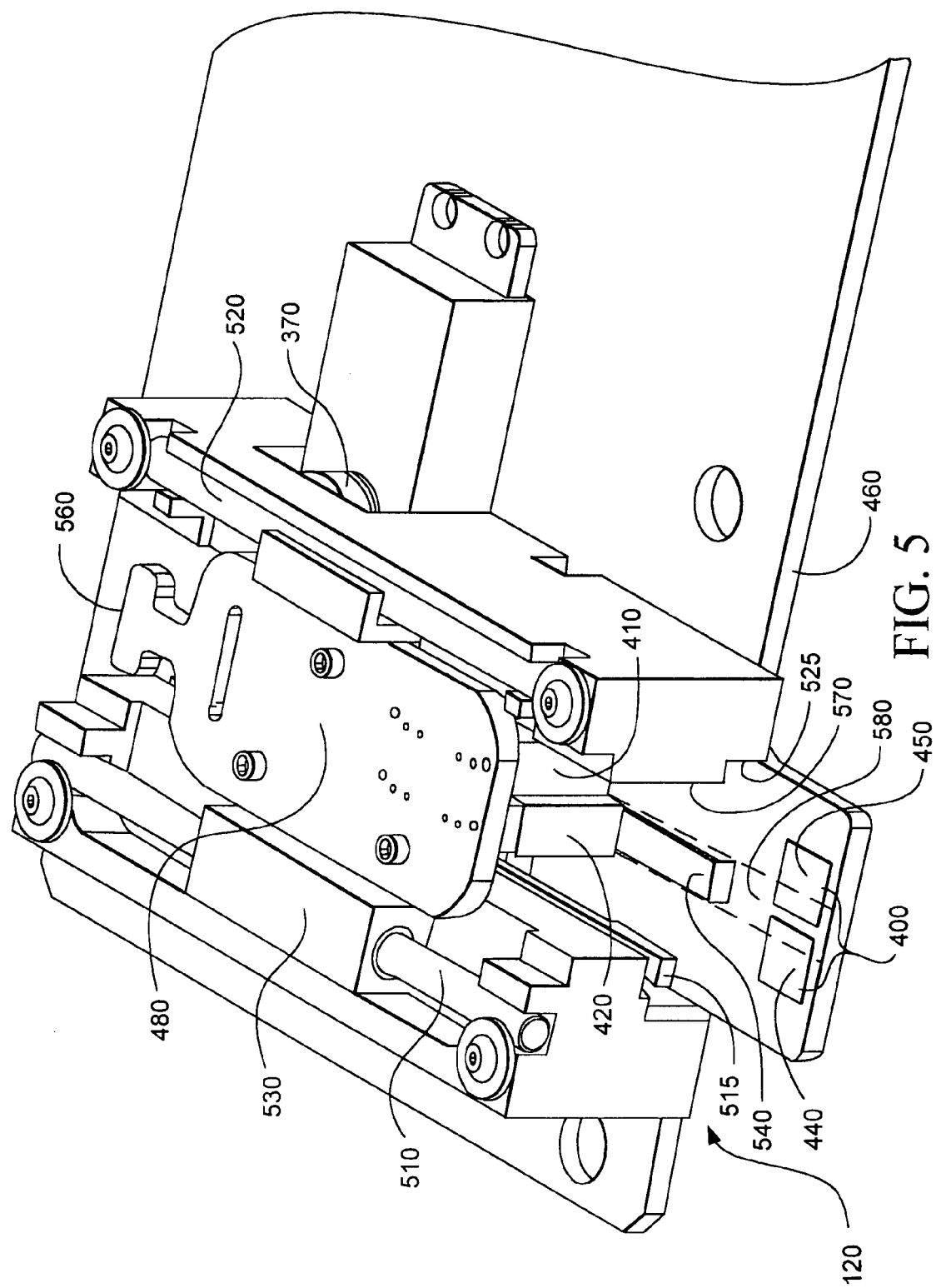
FIG. 5 is a front isometric view of the reader of a preferred embodiment.

FIG. 5 is a front isometric view of the cartridge receptacle 120 further detailing the components therein. As shown, the cartridge receptacle 120 includes a front opening 570 for receiving the cartridge 210, and a back end 560. A left and right receiving structure 515 and 525 for receiving the cartridge 210 extends from the front opening 570 to the back end 560 and in close proximity to the bottom printed circuit board 460. The receiving structures are precisely dimensioned to frictionally fit the front end 215 of the cartridge 210 (as shown by FIG. 2).

The cartridge receptacle 120 preferably includes a motion mechanism for moving a first optical sensor 420 with respect to the test strip 200. To this end, a left and right rail 510 and 520 each mount to a top portion of the respective left and right sidewall 470 and 430, and extend in a longitudinal direction defined by the front opening 570 and back end 560. A sled 530 slidably mounts over the left rail 510 and retains the top printed circuit board 480 that extends to the right rail 520. The first optical sensor 420 and second optical sensor 410 attach to the top printed circuit board 480 extending from the sled 530. The motor 370 engages the sled 530 to longitudinally direct the sled along the rails 510 and 520. The resulting motion of the sled 530 moves the top printed circuit board 480, so that the first optical sensor 420 and second optical sensor 410 also move longitudinally within the cartridge receptacle 120. In this arrangement, the first optical sensor 420 and second optical sensor 410 move over the inserted test strip 200 in performing the assay. This arrangement allows the test strip 200 to remain fixed when the sample is deposited to the application region 260 and flows laterally from the application region 260 to the assay region 250. Alternatively, the motor 370 may be coupled to the cartridge 210 to move the test strip 200 with respect to the sensors. Preferably, the first optical sensor 420 communicates with the computer system through a single element optical sensor, such as a phototransistor or photodiode device. However, multiple array optical sensors such as digital cameras, diode arrays, CCD arrays, or any other photosensitive imaging device may also be employed with this invention, although such multiple array optical sensors add computation cost to the microprocessor.

FIG. 5 also shows that the cartridge receptacle 120 includes a heating element 540 for locally heating the test strip 200. As previously mentioned, the timing and accuracy for performing the assay may be significantly improved by heating the sample during the assay. As shown by the embodiment of FIG. 5, the heating element 540 is a copper or metallic element having sufficient thermal conductive properties to conduct heat to a localized area of the test strip 200. In this manner, the heating element 540 provides for a rapid assay by heating the strip, but not the cartridge receptacle 120. As such, the heating element 540 preserves battery life for field operations, while increasing the speed and accuracy of the assay.

The heating element may be controlled by coupling it to the computer system through associated circuitry (not shown). The associated circuitry may include a temperature feed back control circuit or other sensor, such as a proportional controller or PID controllers, to precisely regulating the temperature of the heating element 540. The computer system may provide the exact temperature and incubation time for switching the heating element on and off. In this manner the heating element 540 may be operated at the optimal temperature and incubation time for a particular assay. As will be described below, the optimal temperature and incubation time for any particular assay may be provided by an assay table stored in the memory resources 310 of the computer system. Accordingly, the heating element 540 of a preferred embodiment may enhance the flexibility of the reader 100 to perform a wide range of assays.

FIG. 5 further details the autostart trigger 400 of a preferred embodiment. The first pad 440 and second pad 450 that comprise the autostart trigger 400 may be any electrical lead, including metal plates or meshes. As shown, the first and second pads 440 and 450 may be mounted in co-planar fashion to the bottom printed circuit board 460. Preferably, the pads combine to form a capacitor, with each pad forming a capacitor plate. In alternative variations, the pads may combine to provide a detectable electrical field that noticeably changes upon deposition of the sample. Upon entrance of the cartridge 210 into the cartridge receptacle 120, the test strip 200 is aligned so that an area under the assay region 250 contacts the heating element 540. Once aligned, the application region 260 is in close proximity to the first pad 440 and second pad 450. The alignment of the test strip 200 is illustrated by the region corresponding to numeral 580. Alternative variations allow the positions of the first and second pads 440 and 450 to be moved away from the bottom printed circuit board 460, as the pads may be positioned anywhere relative to the strip 200 to allow the capacitance or electrical field to be affected by the deposition of the sample. Similarly, the alignment of the pads may be non-coplanar, or even perpendicular, as such alternative positions still produce an electrical field that is affected by the deposition of the sample.

Figure 6:
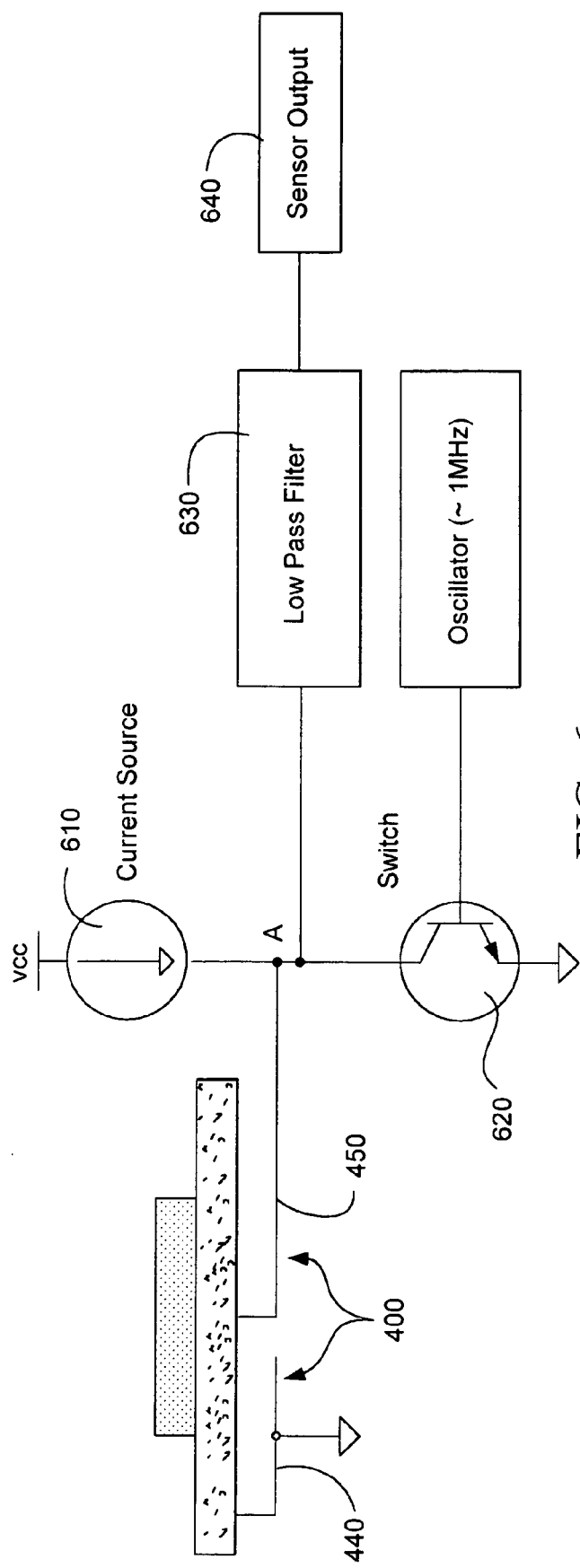
FIG. 6 is a block diagram of an autostart trigger preferred with this invention.

FIG. 6 is a block diagram that details the autostart trigger 400 of a preferred embodiment. The first pad 440 and second pad 450 are arranged on the bottom printed circuit board 460 (FIG. 4) to couple with an electrical potential to form a sensing capacitor for detecting when the sample is deposited onto the application region 260 of the test strip 200. The autostart trigger may couple to the computer system through a sensory output line 640. The signal from the autostart trigger 400 may be amplified prior to being received by the computer system. As shown by a preferred embodiment of FIG. 5, the test strip 200 aligns over a portion of the first pad 440 and second pad 450, with the space between the first and second pad being aligned over the centerline of the test strip 200 (as shown by FIG. 5). The test strip 200 is placed in sufficient proximity to form a portion of the dielectric layer between the capacitor formed by the first pad 440 and second pad 450. Alternatively, the first pad 440 and second pad 450 may abut the bottom portion of the test strip 200. In this arrangement, the first pad 440 and second pad 450 may be coupled to a current source 610 that causes the voltage on the sensing pads to ramp up. A switch 620 may be coupled to the current source 610 to allow the sensing pads 440 and 450 to discharge periodically. The voltage on the first pad 440 and second pad 450 signal a sawtooth waveform, with an average value related to the capacitance between the first and second sensing pads 440 and 450. A low pass filter 630 may be coupled to generate the average value of the voltage on the sensing pads 440 and 450. Prior to the time the sample is deposited, the application region 260 is dry and the dielectric constant formed in part by the test strip 200 is low. When the sample is applied to the application region 260, the dielectric constant is significantly increased, causing a change in the capacitance between the sensing plates. A software algorithm executed by the computer system may then be used to compare the curve of the capacitance versus time across the first pad 440 and second pad 450 to detect the presence of a sample based on a threshold change in the capacitance curve. In alternative variations, depositing the sample induces a change in the electrical fields between the electrical leads. In this manner, the autostart trigger 400 may detect the change in capacitance of the first pad 440 and second pad 450 upon addition of the sample to the application region 260 of the test strip 200. Once the sample is detected by the autostart trigger 400, the computer system initiates timing the assay. Timing the assay allows the assays to be analyzed by the sensors and processor at an exact moment after the sample is deposited. As such, the reader 100 provides an advantage over the known art in that it avoids inaccuracies that result from mis-timing the moment at which the final analysis of the test strip 200 is performed.

Several alternative methods for detecting the change in the capacitance of the pads 440 and 450 exist. For example, the first pad 440 and second pad 450 may be used to form a capacitor element of an inductor-capacitor ("LC") circuit. The LC circuit may be coupled to an oscillator, and associated circuitry may then be implemented to sense the change in capacitance when the fluid sample is added to the application region 260.

In alternative embodiments of the present invention, an autostart trigger may be coupled to or comprises within the reader 100' of the present invention to detect any physical change arising from depositing the sample on the strip. For example, sensors may be coupled to the processor to detect changes in the surface tension of either the strip 200 or of the sample being deposited on the strip. Alternatively, sensors may also couple to the strip to determine the conductivity of the strip before and after the sample is determined. Such sensors may include implementing a voltage potential on one end of the application region 260, and determining the current or voltage on another end of the application region before and after the deposition of the sample to the strip 200. Other alternative variations for autostart triggers may be found in the prior art, such as U.S. Pat. No. 5,554,531 to Zweig, and U.S. Pat. No. 5,580,794 to Allen, both of which are hereby incorporated by reference.

In a preferred embodiment, the autostart trigger 400 generates a continuous waveform that is affected by any change in the dielectric layer or electric field shared between the sensor pads 440 and 450. For example, insertion of the cartridge 210 may interfere with the dielectric layer or electric field between the sensor pads to cause the resulting waveform to change sufficiently to falsely indicate the presence of a sample. Therefore, a preferred embodiment also includes a mechanism that prevents the autostart trigger 400 from signaling the processor until a time delay period after the insertion of the cartridge 210. In a preferred embodiment, the mechanism includes an infrared sensor mounted within the cartridge receptacle 120 that signals the computer system upon insertion of the cartridge 210. The processor 300 may be programmed or otherwise provided with resources to preclude the autostart trigger from signaling the processor of a capacitance change for a time delay period after the insertion of the cartridge 210. The time delay is preferably shorter than the minimum time needed by a user to deposit the sample after the cartridge is inserted. In this manner, the insertion of the cartridge will not falsely signal the processor to initiate the timer for the assay. Rather, the time delay ensures that the timer for the assay will not be signaled until the sample is deposited.

As noted, the reader 100 includes resources such as the processor 300 and memory resources 310 that retain parameters and information for controlling and analyzing the assay. The parameters and fields may be stored in the memory resources 310, and include fields for performing the algorithm that analyzes and interprets the results of the assay. The fields and parameters may be grouped into assay tables, which may be selected according to the particular assay being performed. In this manner, the assay table encodes any combination of fields and parameters for analyzing distinct assays, as well as including fields and parameters to correctly analyze each assay. The assay tables may be reconfigured to provide one or more updated parameters for assays, or to include additional assay tables for new assays. The assay tables may be reconfigured by a combination of the input device 390, serial port 395, and replaceable memory resources 310. Thus, the assay table may be reconfigured in any number of ways, including modifying a single element through the bar code on the cartridge 210 or by uploading an entirely new assay table. A preferred embodiment employs Dallas Buttons as memory resources, which may be easily removed or added to a compartment or surface of the reader 100.

In more detail, the memory resources 310 of a preferred embodiment may include the following parameters as fields included in the assay tables:

ZONELOCATION: This field identifies the location or relative position of the measurement zones on the test strip 200. The field is preferably 15 bits, with each 3 bits identifying a particular measurement zone. The measurement zones may be selected to correspond to either analyte binding zones or control binding zones, thereby allowing the respective zones to be positioned anywhere on the test strip 200 with respect to one another. A preferred embodiment stores five measurement zones on the strip, including measurement zones for three analyte binding zones and two control binding zones. The control binding zones may be high or low control, while each analyte binding zone may include an analyte for one or more assays. The ability of the reader to allow for selection of the position of the measurement zones for the control binding zones and analyte binding zones is particularly advantageous, since the presence of an upstream measurement zone may affect the chemical constituency of a downstream measurement zone during lateral flow. Therefore, the optimal relative position of the control binding zones and the analyte binding zones may differ from assay to assay. A preferred embodiment provides flexibility in ensuring the control and analyte binding zones may be positioned in their optimal position on the test strip 200 for any particular assay.

HIGHCONTROL/LOWCONTROL: These fields specify relative values of the detection signal arising from the high and low control binding zones. The values from these fields may be assigned from the assay table to the algorithm.

ASSAYID: The particular assay table to be employed for the assay is specified by this field. The field is preferably specified from the bar code on the cartridge 210 carrying the test strip 200.

MAXCONTROLRAT/MINCONTROLRAT: These fields specifies the maximum and minimum ratio between the measurement zones corresponding to the high and low control binding zones.

METHODSIZE: This field determines the method for interpreting the results of the assay, and the sample size to be used in the assay. Preferably, the processor 300 internally determines the results of the assay by using a relative intensity curve. Based on the value of this field stored or inputted into the assay table, the results may then be displayed to the user using either signal cut-off value, standard curve, or the relative intensity curve. With the standard or relative intensity curve, the detection signal arising from the measurement zone of the analyte binding zone is quantified from the curve, and then compared to the cut-off value to determine if sufficient analytes exist for a positive reading. The detection signal arising from the measurement zone of the analyte binding zone is divided by the cut-off value to determine the signal-cut-off value. The ability to select or predetermine the method for interpreting any particular assay further enhances the flexibility provided to the user by the reader 100.

KINITICSTARTTIME: This field may be used to specify the time interval beginning with the addition of the sample until the first read occurs.

ASSAYTIME: This field specifies the total assay time in seconds.

ASSAYTEMP: This field specifies the preferred temperature for running a particular assay.

LOWCONTROLMINDR/LOWCONTROLMAXDR: These fields specify the minimum and maximum low control values quantitatively. In a preferred embodiment, the fields are expressed in terms of Density of Reflection (DR), as further described below. If the low control is either below LOWCONTROLMINDR or above LOWCONTROLMAXDR, an error will be provided.

CUTOFFRATIO: This field specifies the cutoff ratio used to determine whether a given measurement zone of an analyte binding zone is positive or negative. This field may be provided in the assay as a predetermined value based on laboratory experimentation. In a preferred embodiment, the field may be altered by the bar code, which provides a multiplication factor for the value of the field stored in the assay table. Alterations in the bar code may then change the cut-off value. As such, the assays are not limited to a strict cut-off value, but rather may provide cut-off values as a variable input to the algorithm. This enables the cut-off values to be altered as the need arises.

The processor 300 uses the assay tables of the memory resources, as well as parameters and fields inputted through the input device 390 and/or serial port 395, to execute an algorithm that accurately analyzes and interprets the results of the assay. The processor may also receive prompts or input information for running the algorithm from the bar codes 230 via the second optical sensor 410.

Figure 7A:
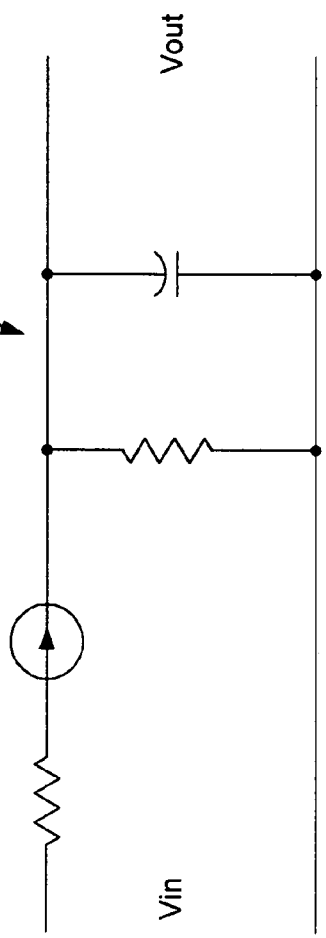
FIG. 7A is a schematic of a model used by the algorithm of a preferred embodiment.
Figure 7:
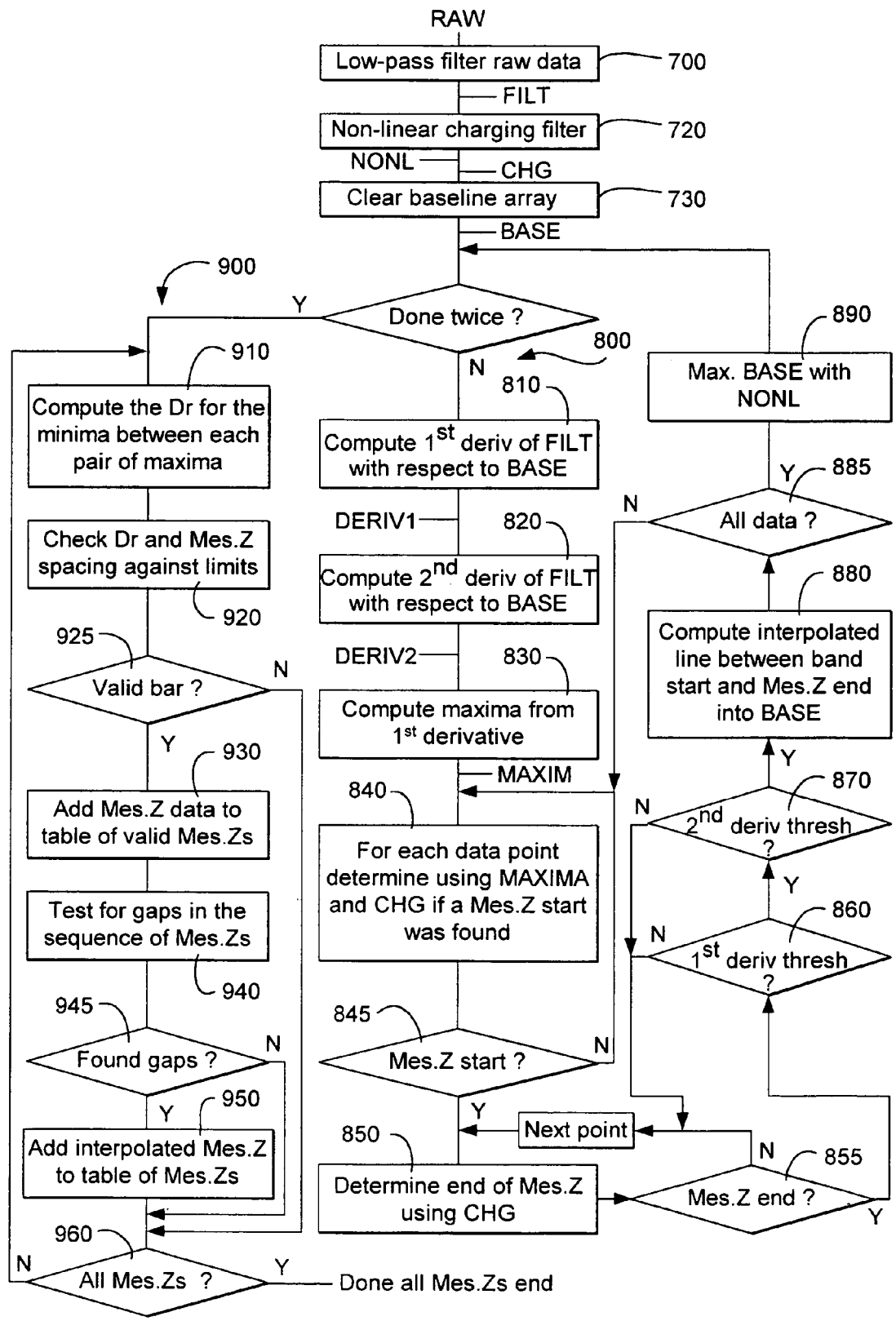
FIG. 7 is a flow chart of an algorithm performed by a preferred embodiment for analyzing results of an assay.

FIG. 7 describes a preferred algorithm performed by the processor 300 in determining the results of the lateral flow assay. The algorithm of this invention analyzes the results of the lateral flow assay by generating a baseline, quantifying the measurement zones with respect to the baseline, and then comparing measurement zones corresponding to the control binding zones and analyte binding zone. The baseline is generated to approximate the signal of the strip 200 as if the measurement zone is not present. In order to attain the most accurate results for a preferred embodiment, the baseline should approximate the reflectance of the test strip 200 after the assay has been performed. However, the baseline of the actual test strip 200 after the performance of the assay is not constant across the strip. Rather, several factors contribute to produce an uneven or spotty baseline. For example, when performing an assay by measuring the reflectance arising from the strip, the reflectance of the baseline may be affected by (1) wave fronts created by the sample which create patches of wet and dry regions along the length of the strip; (2) non-specific binding, which results in the formation of light absorbing particles in between the measurement zones; (3) warpage in the nitrocellulose layer; and (4) manufacturing problems in implementing a flat test strip 200 within the cartridge 210. In addition, when whole blood is used as the sample, the baseline reflection may be affected by red blood cells or hemogloblin.

In several examples provided by the known art, these problems have been avoided by generating a baseline from a dry strip, or inputting the baseline as a known constant into a calculation for evaluating measurement zones. These approximations for the baseline as determined by the known art lack accuracy, however, as the approximations are not from the strip after undergoing the assay. Thus, the baseline incorporated for interpreting assays in the known art fail to account for example, ripples that actually change the reflectance of the strip and thereby affect the results of the assay. Similarly, the known art fails to account for measurement zones containing compounds formed after the sample is deposited on the strip.

Among other advantages, this invention improves in part over the known art by approximating a baseline from the test strip 200 after the assay is performed. The resulting approximation is considerably more accurate for evaluating the measurement zones and comparing the measurement zones to one another. In a preferred embodiment, the algorithm generates the baseline by approximating a relatively flat baseline in detection zones where the intensity of reflectance of the strip is variable with respect to the background of the strip. In particular, the detection zones include measurement zones corresponding to the control binding zones and/or analyte binding zones, which contain concentrated amounts of light absorbing compounds. The algorithm then uses the baseline to quantify or evaluate the measurement zones with respect to the baseline, and then compares the value of each measurement zone to determine the presence of disease. In a preferred embodiment, the measurement zones are quantified by using the baseline to determine the Density of Reflection (DR) of the measurement zone. Alternatively, the measurement zones may be quantified through equations or functions that compare the detection signal arising from the measurement zone with respect to the detection signal arising from the remainder of the test strip. The measurement zones may also be evaluated qualitatively with respect to the baseline, or mapped using the baseline to determine the results of the assay.

In step 700 of the algorithm, the first optical sensor 420 scans or views the test strip 200 and compiles an array of raw data RAW that corresponds to the intensity of the reflectance of the strip. Alternative embodiments of this invention may provide for a sensor that detects detection signals such as fluorescence or radiation. In either case, the array RAW represents voltage counts of the analog-digital converter which may be coupled to the sensor of the particular variation to reflect the intensity of the alternative detection signals. In a successful assay performed under a preferred embodiment that measures reflectance from the strip 200, the measurement zone of the high control zone is relatively darker or less intense in reflectance than the measurement zone of the low control zone due to a greater concentration of light absorbing particles. One or more measurement zones of analyte binding zones may also be present, depending on whether the samples contained analytes. As such, the darkness or reflectance intensity of the analyte binding zones is a variable measurement zone. The array RAW records the reflectance intensity arising from the strip, including the reflectance of the measurement zones. The array RAW is then filtered by a low-pass filter that represents a moving average of the array RAW. The filtered data is retained in the array FILT.

Step 720 shows that a Boolean operation assigns a binary state to the individual elements of FILT. In a preferred embodiment, the Boolean operation is designed to approximate the proximity of the individual array element to an average white reflectance. When the state assigned by the Boolean operation is "true", the individual elements of FILT are termed "white". For purposes of this disclosure, "white" refers to elements that fall within a range of threshold approximations of the average white for the strip. When the Boolean operation is "false", the individual elements of FILT are "dark". The term "dark" refers to elements that are not white, or false under the Boolean condition provided above. Numerous operations may be used with this invention to assign the binary state to the elements of FILT. For example, the Boolean operation may reflect a substantial change between the reflection intensity of adjoining points or a selected block of points.

In a preferred embodiment, the Boolean operation is modeled after a non-linear decay circuit comprising a diode-resistor-capacitor, as shown by a circuit 725 in FIG. 7a. The charging voltage on the capacitor may be modeled after the following equations:

$$Vout_{i+1} = (Vout + Vin)_i / 2 \quad (1)$$

for a charging capacitor; and $$Vout_{i+1} = Vout_i - Vout_i * (1/DF) \quad (2)$$

for a decaying capacitor.

In the above equations, DF represents an exponential or high order decay factor. The value of DF is preferably chosen to match the degree of ripple or other defect observed in actual strips. Large value for DF are appropriate for "good" strips which have fewer ripples, and provides for the best detection of small signals. Smaller values for DF reject larger defects at the expense of reduced ability to distinguish small signals from the baseline. In this model, Vin is provided by FILT, and an array NONL stores Vout. Under a preferred embodiment, when equation (1) is true, elements of FILT are assigned a "white" state in CHG and equation (1) applies in determining NONL. If equation (1) holds to be false, then the elements of FILT are assigned a "dark" state in CHG, and equation (2) applies in determining NONL. Once the CHG and NONL arrays are determined, the array BASE representing the baseline may be formulated. Initially, BASE is set to zero in step 730.

The subroutine 800 generates the baseline approximation for detection zones on the strip based on the information stored in FILT, CHG, and NONL. The first step 810 calculates the derivative of FILT with respect to BASE and stores the values in an array DERIV1. The next step 820 calculates the derivative of DERIV1 with respect to BASE and stores the values in an array DERIV2. In step 830, all maximas and minimas are determined from DERIV1 and stored in an array MAXIM. The elements of MAXIM may be either local maximas/minimas or endpoints to measurement zones that correspond with array elements of FILT. In addition, individual elements of CHG, DERIV1, and DERIV2, correspond to the same elements of FILT.

The algorithm then identifies in step 840 a beginning point to each measurement zone present on the strip. Step 845 of a preferred embodiment shows than an element of MAXIM is a beginning point of a measurement zone if it immediately precedes or is at a location where CHG switches from "white" to "dark". This criteria ensures that the maxima is a beginning point to a measurement zone as opposed to a local maxima or a minima. By properly choosing the DF, most of the local maximas and minimas may be removed from FILT. Once a beginning point is found, step 850 seeks the ending point of the measurement zone by first identifying an element of MAXIM where CHG changes states from "dark" to "white". The algorithm then implements a criteria for determining a subsequent point in a "white" state that is an endpoint to the measurement zone. The criteria may include steps 860 and 870, which determines whether a first and second derivative threshold is met by an element of MAXIM subsequent to the point found in step 850. The first and second derivative thresholds may be implemented as predetermined constants.

Once the endpoint to the measurement zone is found, the algorithm in step 880 interpolates between the beginning and ending points of the measurement zone. The interpolation may be accomplished by connecting the beginning and ending points through a straight line or through some other function that approximates a baseline between the two points. The algorithm also interpolates a baseline in the detection zones encompassing points beyond the measurement zone. Interpolation in the detection zones may be accomplished by connecting the respective maximas and minimas outside of the measurement zone. All interpolated points may then be stored in BASE.

In a preferred embodiment, anywhere between two to five measurement zones may be present on the test strip 200. In step 885, the algorithm checks to see whether all data in FILT has been checked to ensure all measurement zones are located. If additional points are present, the algorithm returns to step 850 to determine whether additional measurement zones exist on the test strip 200. When all values of FILT have been checked, step 890 performs a max BASE with NONL, where corresponding elements of the two arrays are compared, and BASE receives the greater of the two elements. This step serves as another approximation to the baseline generated by the subroutine 800.

The approximation of the baseline may be improved by repeating steps 810 through 890 again, except in the subsequent loop BASE is an approximation of the average baseline of the strip, rather than "0". The second approximation of the baseline differs in that DERIV1 and DERIV2 may be calculated with respect to BASE having values of the average baseline. The resulting baseline is a much smoother approximation of the average baseline for the strip. The subroutine for determining the baseline may be repeated a number of times, but beyond two iterations yields insignificant improvements.

Once the baseline is generated, the algorithm then proceeds to determine the reflection intensity of the strip in subroutine 900 by using FILT and BASE. In step 910 reflection intensity may be calculated by determining the DR, represented by the following formula:

$$DR = \log[(FILT - BLACK)/(BASE - BLACK)]$$

BLACK may be an array of constants that correspond to the reflection of the strip when the light within the cartridge receptacle is turned off. In a preferred embodiment, the DR is calculated only for minimas between each pair of maximas. This allows for the use of a small processor for field uses of the reader. Alternatively, the DR of every element of FILT may be determined with larger processors. In variations of the invention, the difference between the intensity of the detection signal and the baseline may be evaluated using different formulas and criteria. The equation provided above is preferred for reflectance based assays.

In step 920, DR for each determined measurement zone is checked against preselected limits stored in the assay table. This step may include checking parameters such as HIGH CONTROL and LOWCONTROL, MAXCONTROLRAT and MINCONTROLRAT, as well as other parameters that may indicate an error in the assay. The spacing between measurement zones is also checked to conform to the preselected spacing, which in a preferred embodiment is retained in the assay table as MINBANDSPACING and MAXBANDSPACING.

Valid measurement zones are detected in step 925 and recorded in step 930 as a separate sequence. Once all valid measurement zones are recorded, the algorithm checks in step 940 for gaps in the sequence. Instances when gaps may be found include when the sample that lack antigens, i.e. where the assay is negative. If a gap is found in step 945, the gap is interpolated over and added to the table of measurement zones in step 950. The algorithm stops in step 960 once the number of detected measurement zones and gaps matches the number of measurement zones expected by the input to the reader 100. Otherwise, steps 910-960 are repeated.

Figure 8:
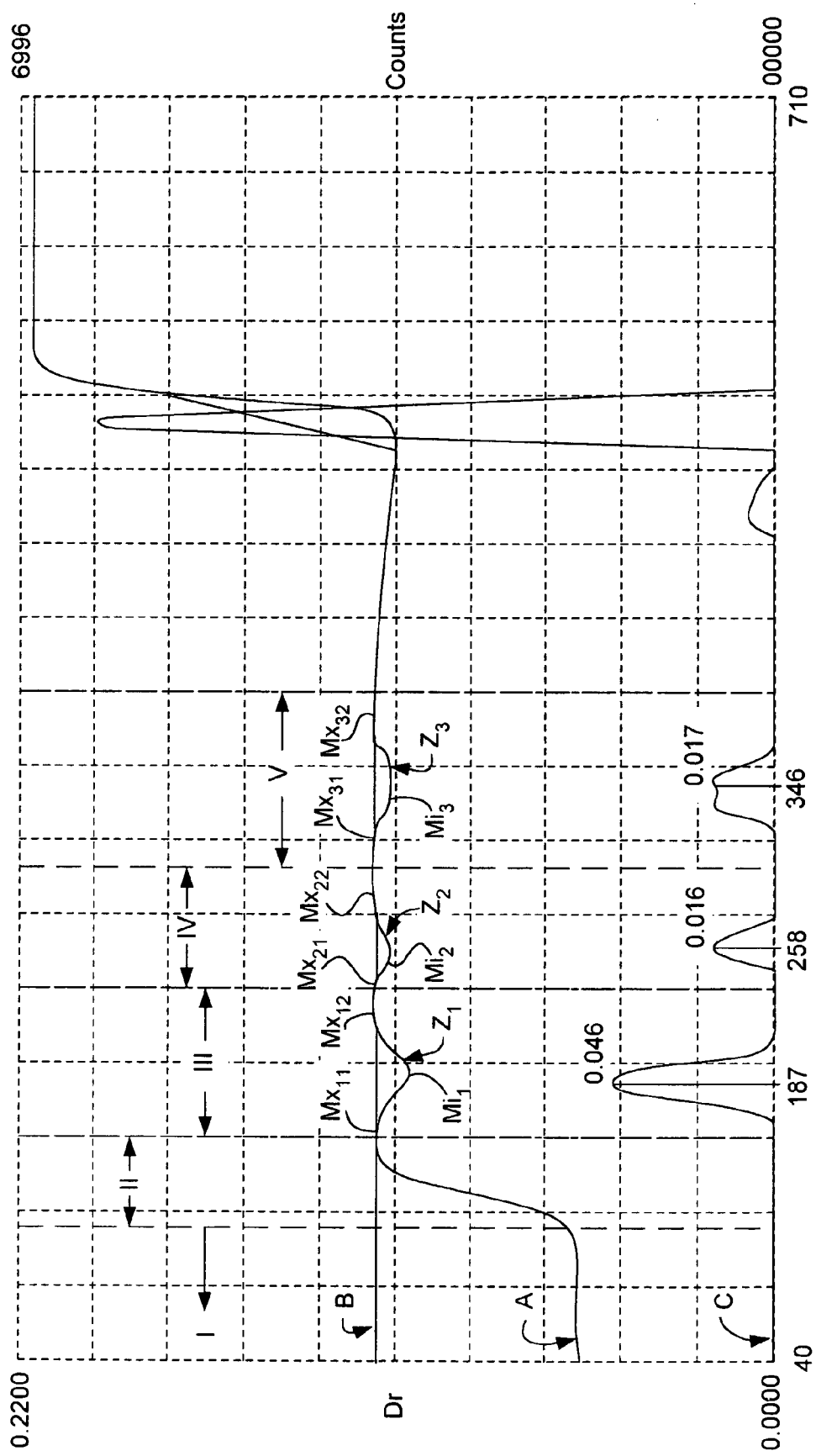
FIG. 8 is an illustrative data graph of the results attained by this invention.

FIG. 8 illustrates a graph of values generated by the algorithm of a preferred embodiment, detailing the generation of the baseline and the evaluation of the measurement zones for the control and analyte binding zones with respect to the baseline. Curve A is derived from FILT, and is a quantified representation of the strip in terms of the voltage count detected from the A/D converter. While the voltage counts of curve A represent reflection intensity arising from the strip, in alternative embodiments, the voltage counts may represent the intensity of any detection signal arising from the strip. In a preferred embodiment, brighter or more reflective surfaces produce a higher count on the graph presented in FIG. 8. In region I, curve A shows the first optical sensor 420 as being away from the test strip 200. In region II, the optical sensor scans a shadow region formed by the edge of the exposed test strip 200 and the cartridge 110. The shadow region may be used by the processor to synchronize the first optical sensor 420 with the location of the measurement zone for the control and/or analyte binding zones. The values of DERIV1 are generally greater in the shadow region due to the lack of reflection. Once the derivative of curve A is determined to exceed a predetermined threshold value corresponding to the slope of the shadow region, the position of the optical sensor is then marked as the beginning of the test strip 200.

Region III of curve A contains a measurement zone Z1 present on the test strip 200. The algorithm detects the beginning point Mx11 and ending point Mx12 of the measurement zone Z1. Each beginning and ending point is contained within region III and just outside the measurement zone Z1, where the reflection of the measurement zones become noticeably different than the average background reflection. As illustrated by curve A, the beginning point Mx11 is a maxima on the curve A that is subsequently followed by curve A changing from a "white" state to a "dark" state. As previously noted, the change of state is stored in CHG. A minima Mi11 is the point between the beginning and ending points Mx11 and Mx12, and represents an area of the measurement zone having the least reflection or lowest-count. The maxima Mx12 follows curve A changing state from "dark" to "white" and meets the threshold test of steps 860 and 870 of the algorithm of FIG. 7. Curve B shows a baseline generated from the algorithm of a preferred embodiment to further quantify curve A. The baseline matches the filtered points of curve A outside of the measurement zone Z1. Inside the measurement zone Z1, a function connects the beginning and ending points Mx11 and Mx12 to form the baseline. Preferably, the function is a straight line between the two points, although other functions may be used.

Regions IV and V produce measurement zones Z2 and Z3, corresponding to additional measurement zones present on the strip. As with measurement zone Z1, the baseline represented by curve B may be interpolated between beginning points Mx21, Mx31 and ending points Mx22, Mx32 of respective measurement zones Z2 and Z3. Likewise, each measurement zone Z2 and Z3 includes a minima Mi22, Mi33 which represents the area of the respective measurement zone having the least reflective properties.

As shown by FIG. 8, measurement zones Z1 and Z2 correspond to high and low control binding zones on the test strip, and measurement zone Z3 corresponds to the analyte binding zone. A preferred embodiment may be employed with the assay tables stored in the memory resources 310 to provide flexibility in performing the assay and analyzing the results. In particular, the location of the particular zones may be controlled by ZONELOCATION, so that measurement zone Z1 or Z2 may alternatively represent the analyte binding zone. The values of measurement zones Z1 and Z2 may be controlled by HIGHCONTROL and LOWCONTROL. The ratio between Z1 and Z2 may be limited by MAXCONTROLRAT and MINCONTROLRAT. The field SPACING may be used to provide for the relative distance between the measurement zones.

Curve C represents curve A quantified with respect to curve B. In a preferred embodiment, curve C is determined by approximating the DR in the measurement zones, using values of curve A corresponding to FILT and curve B corresponding to BASE. The DR of each measurement zone may be determined by determining the DR of the minima for each measurement zone. Alternatively, the DR for each element of FILT represented by curve A may be determined with respect to curve B and BASE. The output may be represented through a relative intensity curve. In FIG. 8, the ratio of values for the high and low control represented by measurement zones Z1/Z2 is approximately three. The value of the measurement zone Z3 representing the analyte binding zone is determined relative to the values for the measurement zones Z1 and Z2. In this method, the values of the respective measurement zones may be determined in terms of RI.

In a preferred embodiment, the reader 100 will provide a "positive" result to the user if the value of measurement zone Z3 representing the analyte binding zone is greater than the cut-off value. The cut-off value may be altered between the assays by multiplying CUTOFFRATIO by a factor inputted into the processor 300 by the bar code or other input device.

From the above description, the algorithm of a preferred embodiment may include (1) a peak detector based on digital implementation of a Boolean function, such as the analog diode-RC combination shown in FIG. 7a; (2) a non-linear interpolation of maxima using information from the first and second derivatives, where the information is derived from raw data recording the intensity of detection signals arising from the strip 200; and (3) repeating step (2) for further accuracy.

While a preferred embodiment may use the methods presented above, other methods may also generate a baseline across a test strip undergoing or having undergone an assay. In general, other methods presented below have fewer advantages than the methods described above, in that the methods below may require additional computational costs, lack precision, and may be limited in applications or diversity. These other methods may include employing a peak detector to detect the maximas/minimas of the data representing the detection signals from the test strip 200, where the peak detector is symmetrically employed to evaluate the values of the detection signal in a first direction across the strip, and then employed again to evaluate the values of the detection signals in the reverse direction to the first direction across the strip. Such a filter is more appropriate when the data representing the values of the detection signal is symmetrical with respect to a front and back end of the assay region of the strip 200. Such a peak detector would no longer require an array such as CHG, because the Boolean values stored in that array lack the asymmetry that requires the use of first and second derivative thresholds to disambiguate the light/dark transitions. A change to a symmetric filter would eliminate some steps in the non-linear interpolation, and achieve comparable results at the expense of modest increases in computational complexity.

Several other classes of filter are also possible which do not require an "analog" circuit model as described elsewhere in the application. In addition, an interpolation step based on "peaks" from the peak detector rather than "maxima" is possible. Such an interpolation would be sub-optimal, as it would tend to over-estimate the baseline and thus over-estimate the DRs when the general trend of the data is rising or falling. However, one possible advantage of such a method would be to avoid the use of derivatives entirely.

Still further, other variations to a preferred embodiment using the methods described above for generating a baseline include using a peak minima when excessive band widths are encountered to detect a peak pair where the gap between peaks does not return to the baseline. This step may be employed by providing a table of minima from the first derivative to be assembled.

The foregoing description of preferred embodiments of the present invention has been provided for the purposes of illustration and description. It is not intended to be exhaustive or to limit the invention to the precise forms disclosed. Obviously, many modifications and variations will be apparent to practitioners skilled in this art. The embodiments were chosen and described in order to best explain the principles of the invention and its practical applications, thereby enabling others skilled in the art to understand the invention for various embodiments and with various modifications as are suited to the particular use contemplated. It is intended that the scope of the invention be defined by the following claims and their equivalents.

What is claimed is:

1. An apparatus useful for detecting the addition of a sample to a test strip in a lateral flow assay comprising:
   a housing having a receptacle for retaining a test strip for a lateral flow assay; and
   an autostart means;
   wherein the autostart means comprises a capacitance sensor that senses a change in capacitance when a sample or buffer is applied to the test strip in the receptacle, and initiates timing of the assay, and a means for regulating voltage across the capacitance sensor.

2. The apparatus of claim 1, further comprising a heating element positioned to lie under and contact the test strip when the test strip is in place.

3. The apparatus of claim 1, further comprising a test strip.

4. The apparatus of claim 3, wherein the test strip contains a biological sample.

5. The apparatus of claim 4, wherein the biological sample is selected from the group consisting of whole blood, serum, plasma, and urine.

6. The apparatus of claim 4, wherein the biological sample is a human biological sample.

7. The apparatus of claim 4, wherein the biological sample is a non-human biological sample.

8. The apparatus of claim 7, wherein the non-human biological sample is a sample consisting of a livestock and a food product.

9. The apparatus of claim 1, further comprising an optical sensor aligned with the test strip in the receptacle.

10. The apparatus of claim 9 further comprising a moving mechanism attached to the optical sensor that moves the optical sensor with respect to the test strip.

11. The apparatus of claim 9 further comprising a moving mechanism attached to the housing that moves the test strip with respect to the optical sensor, wherein the housing is a cartridge.

12. The apparatus of claim 1, further comprising a sensor that detects the insertion of the housing, wherein the housing is a cartridge.

13. The apparatus of claim 12, wherein the sensor is an infrared sensor.

* * * * *